United States Patent
Burr, Jr.

(10) Patent No.: US 8,006,708 B1
(45) Date of Patent: Aug. 30, 2011

(54) MULTI-COLORED DENTAL FLOSS AND ASSOCIATED METHOD

(76) Inventor: Kenneth M. Burr, Jr., Thorofare, NJ (US)

( * ) Notice: Subject to any disclaimer, the term of this patent is extended or adjusted under 35 U.S.C. 154(b) by 787 days.

(21) Appl. No.: 11/894,489

(22) Filed: Aug. 21, 2007

Related U.S. Application Data (60) Provisional application No. 60/822,969, filed on Aug. 21, 2006.

(51) Int. Cl.
*A61C 15/00* (2006.01)
(52) U.S. Cl. .......................... 132/323; 132/321
(58) Field of Classification Search .............. 132/321, 132/323, 324, 325
See application file for complete search history.

(56) References Cited

U.S. PATENT DOCUMENTS

| | | | |
|---|---|---|---|
| 3,897,796 A * | 8/1975 | Erickson | 132/321 |
| 5,365,874 A | 11/1994 | Dorfman | |
| 6,016,816 A | 1/2000 | Ariagno | |
| 6,145,516 A | 11/2000 | Guay | |
| 6,651,676 B1 * | 11/2003 | Hekimian | 132/321 |
| 2002/0139386 A1 * | 10/2002 | Ochs et al. | 132/321 |
| 2005/0257806 A1 * | 11/2005 | Hay et al. | 132/321 |

* cited by examiner

*Primary Examiner* — Rachel Steitz (57) ABSTRACT

A multi-colored dental floss includes a unitary and flexible core member with an elongated shape provided with opposed first and second ends. The second end is covered by a multi-colored outer coating surrounding an entire circumference thereof, and the first end is an exposed outer surface spaced from the multi-colored outer coating such that the beginning segment remains uncolored. An housing is provided with a bottom cavity, a planar top surface spanning across an entire top side of the cavity, a cutting implement directly attached to the top surface and nested within a first one of the apertures, and a lid pivotally attached to the top surface. The multi-colored dental floss further includes a spool statically seated within the housing, and the core member is concentrically wound about the spool and channeled upwardly therefrom.

18 Claims, 7 Drawing Sheets

MULTI-COLORED DENTAL FLOSS AND ASSOCIATED METHOD

CROSS REFERENCE TO RELATED APPLICATIONS

This application claims the benefit of U.S. Provisional Application No. 60/822,969, filed Aug. 21, 2006, the entire disclosures of which are incorporated herein by reference.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This invention relates to dental floss and, more particularly, to multi-colored dental floss for notifying a user of an end portion of the dental floss.

2. Prior Art

Brushing one's teeth is one of the most important parts of healthy hygiene. In addition to freshening the breath and strengthening the teeth, proper brushing also kills the germs and bacteria that can grow inside the mouth. Recently, the Office of the Surgeon General released its first ever report on the oral health of America and the results were surprising. According to the report, the most common chronic childhood disease by far in this country is tooth decay. In fact, American children lose a staggering 512 million school hours a year due to dental related illness.

Adults also suffer from various forms of dental disease and these complications can lead to painful oral surgeries and costly trips to the dentist. A booming industry, the national health expenditures for dental services exceeded sixty billion dollars in the year 2003. While the Office of the Surgeon General reports that there have been vast improvements in the past fifty years regarding oral health issues, much can still be done in this area. Health professionals maintain that through education and a concerted effort, the number of adults and children suffering from dental disease can be significantly reduced.

To have a healthy smile, the American Dental Association recommends that teeth should be brushed at least twice daily. In addition to brushing, daily flossing has been the prescription for healthy teeth and gums offered by dental hygienists for over 80 years. While flossing is not as widespread as it should be due to what some perceive as challenges, from bleeding gums to dexterity difficulties to the time-consuming nature of the practice, most consumers endeavor to complete this necessary regimen and try to keep floss at the ready whenever they brush their teeth. However, even people who floss conscientiously encounter a frustrating challenge.

Particularly, since the typical packaging of dental floss involves a ball or collection of the string ensconced within a closed container, it can be almost impossible to tell when one is about to reach the string's end. As many consumers would readily attest, there is little more annoying than beginning to floss, only to discover there is only about two or three inches of string left to do the job. Unfortunately, these individuals have no choice but to go to the store immediately for more floss or put off the regimen until a more practical time. Obviously, is would be advantageous to provide a means for a convenient solution to the aforementioned problem.

U.S. Pat. No. 5,365,874 to Dorfman discloses an indicator of the end of a length of a tape of dental floss contained within a dispenser. The indicator is a segment of the length of tape having a different indicia or appearance than a prior segment of the length of tape. The indicator is located at a predetermined distance from an end of the tape to indicate that the length of the tape remaining within the dispenser is being depleted. Unfortunately, this prior art example does not provide several indicators to a user for establishing exactly how much dental floss remains.

U.S. Pat. No. 6,016,816 to Ariagno discloses a process for making a multi-colored dental floss formed of a plurality of bundles of fibers comprising. The process includes: knitting the floss into a tube shape, flattening the tube, printing both surfaces of the flattened tube with a sequence of colored stripes, and unknitting the floss. Unfortunately, this prior art example does not provide several indicators to a user for establishing exactly how much dental floss remains.

U.S. Pat. No. 6,145,516 to Guay discloses a dental hygiene article, including a dental floss, and a microcapsule associated with a portion of the floss. The microcapsule includes a pigment encapsulated within the microcapsule for changing the color of a portion of the floss associated with the microcapsule upon rupture of the microcapsule as an indication of use or release of an active agent. Unfortunately, this prior art example does not provide several indicators to a user for establishing exactly how much dental floss remains.

Accordingly, the present invention is disclosed in order to overcome the above noted shortcomings. The present invention satisfies such a need by providing an apparatus that is convenient and easy to use, lightweight yet durable in design, and designed for notifying a user of an end portion of the dental floss. Multi-colored dental floss uses simple color codes to indicate that the end of a string is approaching, and thereby eliminates the frustration that occurs when a user discovers that there is not enough floss remaining to sufficiently complete a regimen. The present invention offers an easy reminder that facilitates keeping plenty of fresh dental floss on hand at all times. The present invention is simple to use and inexpensive.

BRIEF SUMMARY OF THE INVENTION

In view of the foregoing background, it is therefore an object of the present invention to provide an apparatus for notifying a user of an end portion of the dental floss. These and other objects, features, and advantages of the invention are provided by multi-colored dental floss.

A multi-colored dental floss includes a unitary and flexible core member with an elongated shape provided with opposed first and second ends. Such a first end effectively defines a beginning segment of the core member and such a second end defines an ending segment of the core member. The second end is covered by a multi-colored outer coating surrounding an entire circumference thereof, and the first end has an exposed outer surface spaced from the multi-colored outer coating such that the beginning segment remains uncolored. The core member has an annular cross-section extending along an entire longitudinal length thereof.

The multi-colored outer coating is conveniently impregnated with a plurality of colored agents juxtaposed along a longitudinal length of the second end. The multi-colored outer coating has a uniform thickness concentrically situated about the core member and is directly engaged with the core member and continuously extends along the second end such that the core member is invisible along the second end. The multi-colored outer coating is further formed from at least two separate color dyes evenly distributed along an entire length of the second end.

The multi-colored dental floss further includes a housing provided with a bottom cavity. Such an housing further includes a planar top surface spanning across an entire top side of the cavity. Such a planar top surface is advantageously provided with a plurality of apertures formed therein. The core member is directed through the first aperture and travels along the top surface towards the second aperture. The housing further includes a cutting implement directly attached to the top surface and nested within a first one of the apertures. Such a cutting implement is effectively located downstream of a second one of the apertures and further includes an orifice formed therein such that a continuous passageway is formed between the cavity and an exterior of the top surface for collecting particulate portions of the multi-colored dental floss after is separated by the cutting implement. The housing further includes a lid pivotally attached to the top surface.

The multi-colored dental floss further includes a spool statically seated within the housing, and the core member is concentrically wound about the spool and conveniently channeled upwardly therefrom.

A method for notifying a user of an end portion of a dental floss includes the steps of providing a unitary and flexible core member with an elongated shape provided with opposed first and second ends. Such a first end defines a beginning segment of the core member and such a second end defines an ending segment of the core member. The steps further include covering the second end with a multi-colored outer coating surrounding an entire circumference thereof. The first end has an exposed outer surface spaced from the multi-colored outer coating such that the beginning segment remains uncolored. The core member has an annular cross-section extending along an entire longitudinal length thereof. The steps further include impregnating the multi-colored outer coating with a plurality of colored agents juxtaposed along a longitudinal length of the second end.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

DETAILED DESCRIPTION OF THE INVENTION

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numbers refer to like elements throughout the figures.

The apparatus of this invention is referred to generally in FIGS. 1-7 by the reference numeral 10 and is intended to protect multi-colored dental floss. It should be understood that the apparatus 10 may be used to color code many different types of floss and should not be limited in use with only those types of floss mentioned herein.

Referring initially to FIGS. 3, 5, 6 and 7, a multi-colored dental floss includes a unitary and flexible core member 20 with an elongated shape provided with opposed first and second ends 21, 22. Such a first end 21 defines a beginning segment 26 of the core member 20 and such a second end 22 defines an ending segment 27 of the core member 20. The second end 22 is covered by a multi-colored outer coating 23 surrounding an entire circumference thereof, and the first end 21 has an exposed outer surface 24 spaced from the multi-colored outer coating 23 which is essential such that the beginning segment 26 remains uncolored. The core member 20 has an annular cross-section 25 extending along an entire longitudinal length thereof. The core member 20 is essentially the spool of color coded dental floss.

The multi-colored outer coating 23 is impregnated with a plurality of colored agents juxtaposed along a longitudinal length of the second end 22. The multi-colored outer coating 23 has a uniform thickness concentrically situated about the core member 20 and is directly engaged, without the use of intervening elements, with the core member 20 and continuously extends along the second end 22 which is important such that the core member 20 is invisible along the second end 22. The multi-colored outer coating 23 is further formed from at least two separate color dyes evenly distributed along an entire length of the second end 22. At least two separate color dyes are used in order to ensure that a user is given more than substantial time to purchase more dental floss.

Suitable dyes for creating the multi-colored floss are Food Grade, as approved by the U.S. Food and Drug Administration (FDA). Such dyes include but are not limited to Warner Jenkinson 05601 FD&C Blue #1, D2541 U.S. Purple, FDC.Red #3, 06503 FD&C Green #3, and K7059 degree, D&C Yellow#10. To these food grade dyes may be added antiwick powder sold by Tri-Tex Co. Inc. of St. Eustache Quebec, to control the viscosity of the dye, and an anti-static lubricant, such as Syntholube G from TriTex Co. Inc. The pH of the dye solutions needs to be adjusted to stay in the range of approximately 3, with Citric acid, which is approved by the U.S. FDA, to ensure that the floss is permanently dyed, and the color does not wash out of the floss. Such pH adjustment is made by adding citric acid to the dye formulation. At a pH of 3 the dye strikes best and the color fastness is obtained by steaming the floss at approximately 213 degrees Fahrenheit to impregnation of dye and chemicals. Steaming time is dependant on depth of shade, but should be no less than 5-6 minutes. Steaming also sterilizes the floss. Colors are applied by passing the body through several engraved printing rolls. As known by one skilled in the art, the configuration of the rolls is designed to not overlap the colors, other than by design.

Finishing operations may be performed, such as for example addition of a flavor and/or wax coating. Flavoring is performed applying a cold process, with natural flavors known per se. Wax coating can employ microcrystalline or natural waxes which account for about 2 10% of the thread weight. For example, a wax coating may be applied to the floss by known techniques of drawing the floss through the hot mixture which may be microcrystalline wax or possibly blanched natural bee's wax. Following the wax coating, in the manufacturing phase the thread continues its journey along an artificially elongated path, to allow cooling of the wax, and is then wound on a large storing bobbin.

Referring to FIGS. 1, 2, 3, 4, 5 and 6, the multi-colored dental floss further includes a housing 28 provided with a bottom cavity 29. Such an housing 28 further includes a planar top surface 30 spanning across an entire top side of the cavity 29. Such a planar top surface 30 is provided with a plurality of apertures 31, 32 formed therein. The core member 20 is directed through the first aperture 31 and travels along the top surface towards the second aperture 32. The housing 28 further includes a cutting implement 33 directly attached, without the use of intervening elements, to the top surface 30 and nested within a first one of the apertures 31. Such a cutting implement 33 is located downstream of a second one of the apertures 32 and further includes an orifice 34 formed therein which is vital such that a continuous passageway 35 is formed between the cavity 29 and an exterior of the top surface 30 for collecting particulate portions of the multi-colored dental floss after it is separated by the cutting implement 33. The housing 28 further includes a lid 36 pivotally attached to the top surface 30. The housing 28 encases the core member 20 and the cutting implement 33 allows a user to remove the required amount of floss from the core member 20.

Figure 1:
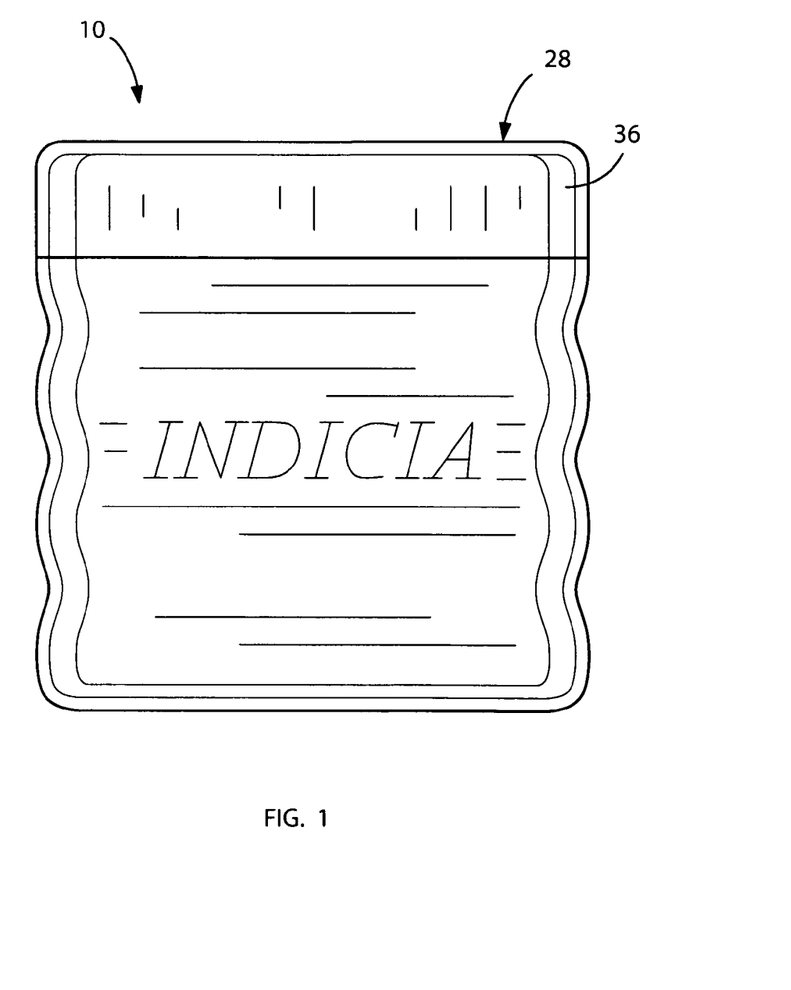
FIG. 1 is a front elevational view of the housing, in accordance with the present invention.
Figure 2:
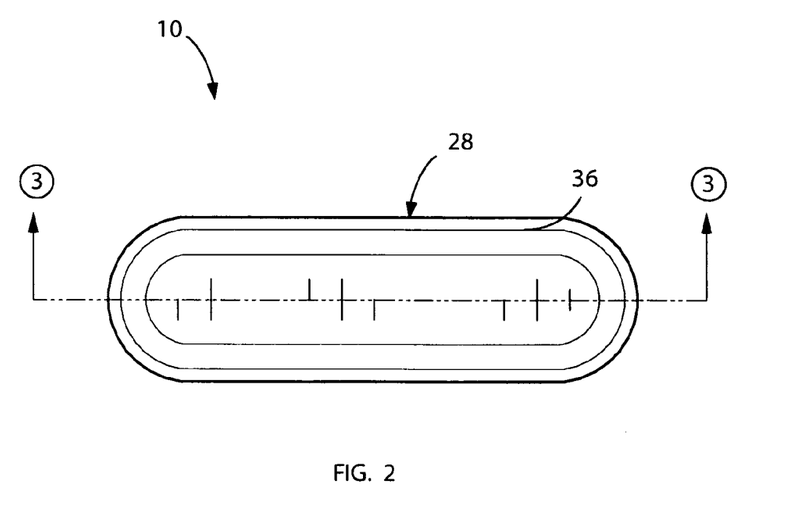
FIG. 2 is a top planar view of the housing, in accordance with the present invention.
Figure 3:
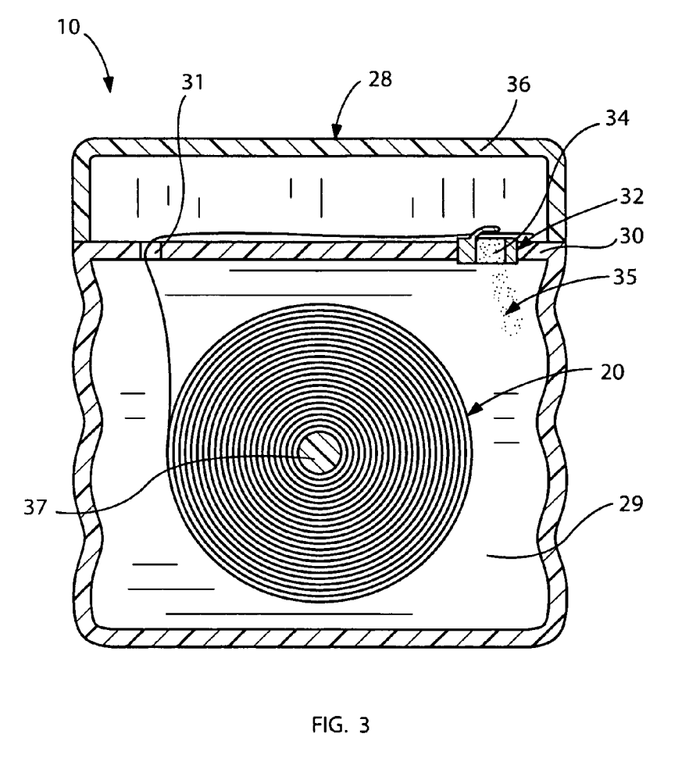
FIG. 3 is a cross sectional view, taken along line 3-3, as seen in FIG. 2.
Figure 4:
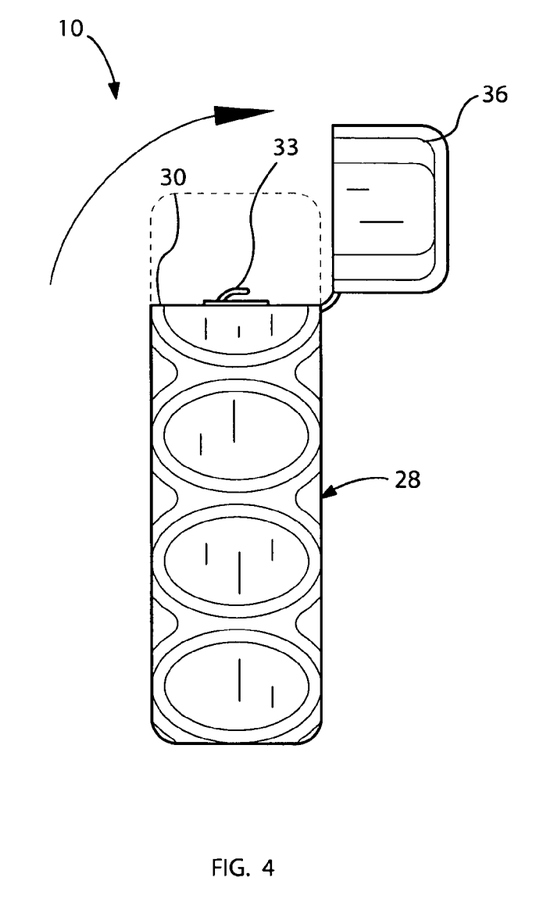
FIG. 4 is a side elevational view of the housing, in accordance with the present invention.
Figure 5:
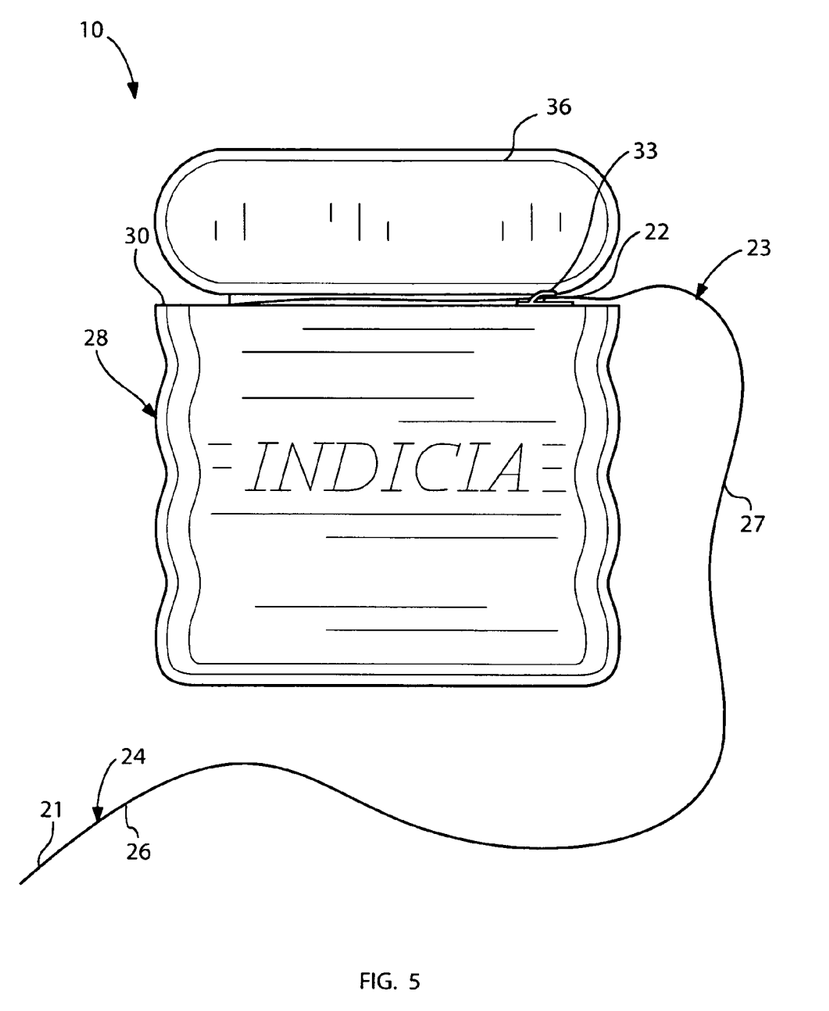
FIG. 5 is a front elevational view of the housing, with the lid open, in accordance with the present invention.
Figure 6:
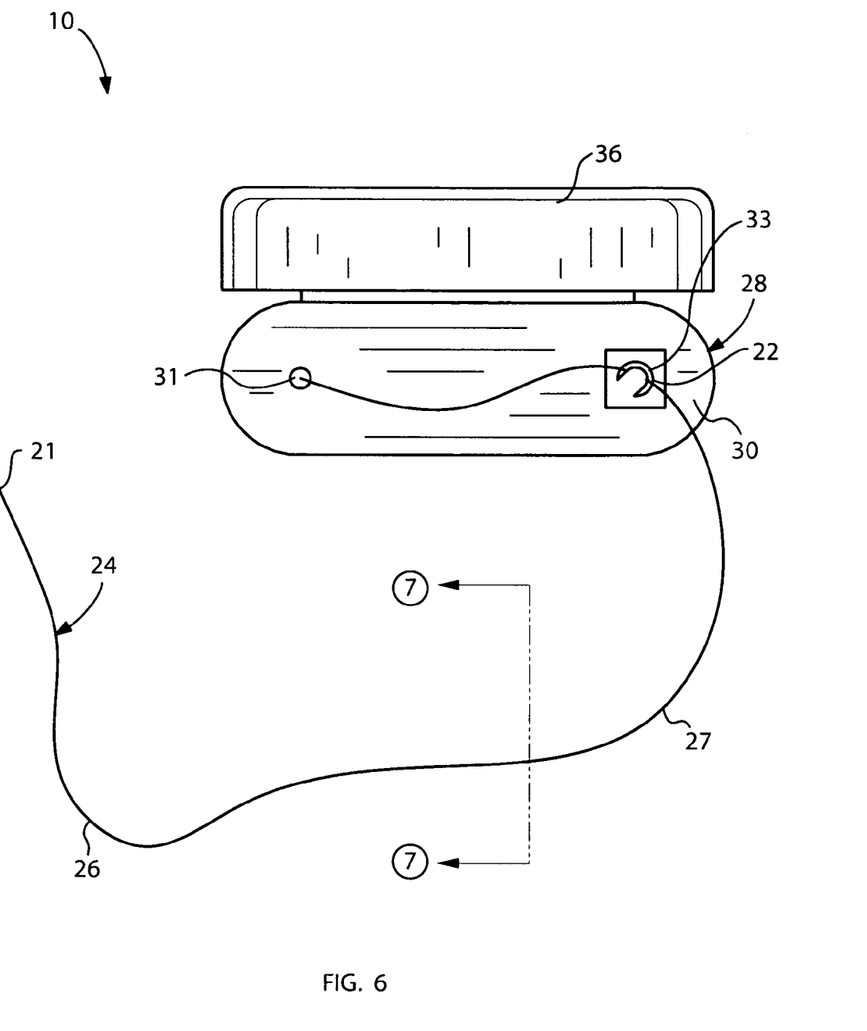
FIG. 6 is top planar view of the housing, with the lid open, in accordance with the present invention.
Figure 7:
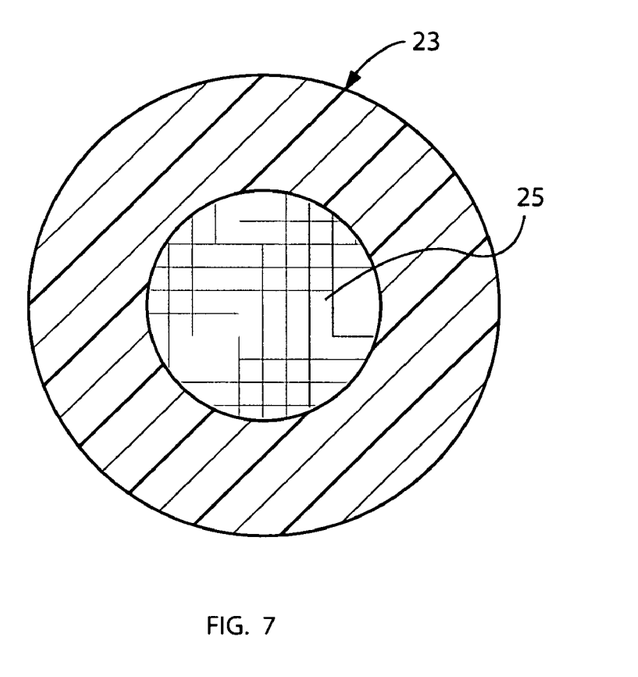
FIG. 7 is a cross sectional view, taken along line 7-7, as seen in FIG. 6.

Referring to FIG. 3, the multi-colored dental floss further includes a spool 37 statically seated within the housing 30, and the core member 20 is concentrically wound about the spool 37 and channeled upwardly therefrom. The spool 37 allows the core member 20 to move freely and easily within the housing during use.

In use, multi-colored dental floss is simple and straightforward to operate. After removing the floss from its sterile plastic packaging, a user pulls a length and flosses in the usual manner. When the floss is yellow, a user is informed that only about a quarter of the floss remains. A user then knows that they must purchase more floss soon. When a user reaches the red section of the floss, the user is informed that the floss will run out very soon and more must be purchased immediately.

The two dye pigments provide the unexpected benefit of providing a user substantial warning before the floss runs out, and an additional warning when a user reaches the very end of the floss. Such a benefits overcomes the prior art shortcomings.

In use, a method for notifying a user of an end portion of a dental floss includes the steps of providing a unitary and flexible core member 20 with an elongated shape provided with opposed first and second ends 21, 22. Such a first end 21 defines a beginning segment 26 of the core member 20 and such a second end 22 defines an ending segment 27 of the core member 20. The steps further include covering the second end 22 with a multi-colored outer coating 23 surrounding an entire circumference thereof. The first end 21 has an exposed outer surface spaced from the multi-colored outer coating 23 such that the beginning segment 26 remains uncolored. The core member 20 has an annular cross-section 25 extending along an entire longitudinal length thereof. The steps further include impregnating the multi-colored outer coating 23 with a plurality of colored agents juxtaposed along a longitudinal length of the second end 22.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

In particular, with respect to the above description, it is to be realized that the optimum dimensional relationships for the parts of the present invention may include variations in size, materials, shape, form, function and manner of operation. The assembly and use of the present invention are deemed readily apparent and obvious to one skilled in the art.

What is claimed as new and what is desired to secure by Letters Patent of the United States is:

1. A multi-colored dental floss for notifying a user of an end portion of said dental floss, said multi-colored dental floss comprising:
    a flexible core member having an elongated shape provided with opposed first and second ends, said first end defining a beginning segment of the core member and said second end defining an ending segment of the core member, said second end being covered by a multi-colored outer coating surrounding an entire circumference thereof, said first end having an exposed outer surface spaced from said multi-colored outer coating such that said beginning segment remains uncolored;
    wherein said multi-colored outer coating is impregnated with a plurality of colored agents juxtaposed along a longitudinal length of said second end.

2. The multi-colored dental floss of claim 1, wherein said multi-colored outer coating has a uniform thickness concentrically situated about said core member.

3. The multi-colored dental floss of claim 1, wherein said multi-colored outer coating is directly engaged with said core member and continuously extends along said second end such that said core member is invisible along said second end.

4. The multi-colored dental floss of claim 1, wherein said multi-colored outer coating is formed from at least two separate color dyes evenly distributed along an entire length of said second end.

5. The multi-colored dental floss of claim 1, further comprising:
    a housing providing with a bottom cavity; and
    a spool statically seated within said housing, said core member being concentrically wound about said spool and channeled upwardly therefrom.

6. The multi-colored dental floss of claim 5, wherein said housing further comprises:
- a planar top surface spanning across an entire top side of said cavity, said planar top surface being provided with a plurality of apertures formed therein;
- a cutting implement directly attached to said top surface and nested within a first one of said apertures, said cutting implement being located downstream of a second one of said apertures and further including an orifice formed therein such that a continuous passageway is formed between said cavity and an exterior of said top surface for collecting particulate portions of said multi-colored dental floss after being separated by said cutting implement; and
- a lid pivotally attached to said top surface;
- wherein said core member is directed through said first aperture and travels along said top surface towards said second aperture.

7. A multi-colored dental floss for notifying a user of an end portion of said dental floss, said multi-colored dental floss comprising:
- a unitary and flexible core member having an elongated shape provided with opposed first and second ends, said first end defining a beginning segment of the core member and said second end defining an ending segment of the core member, said second end being covered by a multi-colored outer coating surrounding an entire circumference thereof, said first end having an exposed outer surface spaced from said multi-colored outer coating such that said beginning segment remains uncolored, said core member having an annular cross-section extending along an entire longitudinal length thereof;
- wherein said multi-colored outer coating is impregnated with a plurality of colored agents juxtaposed along a longitudinal length of said second end.

8. The multi-colored dental floss of claim 7, wherein said multi-colored outer coating has a uniform thickness concentrically situated about said core member.

9. The multi-colored dental floss of claim 7, wherein said multi-colored outer coating is directly engaged with said core member and continuously extends along said second end such that said core member is invisible along said second end.

10. The multi-colored dental floss of claim 7, wherein said multi-colored outer coating is formed from at least two separate color dyes evenly distributed along an entire length of said second end.

11. The multi-colored dental floss of claim 7, further comprising:
- a housing providing with a bottom cavity; and
- a spool statically seated within said housing, said core member being concentrically wound about said spool and channeled upwardly therefrom.

12. The multi-colored dental floss of claim 11, wherein said housing further comprises:
- a planar top surface spanning across an entire top side of said cavity, said planar top surface being provided with a plurality of apertures formed therein;
- a cutting implement directly attached to said top surface and nested within a first one of said apertures, said cutting implement being located downstream of a second one of said apertures and further including an orifice formed therein such that a continuous passageway is formed between said cavity and an exterior of said top surface for collecting particulate portions of said multi-colored dental floss after being separated by said cutting implement; and
- a lid pivotally attached to said top surface;
- wherein said core member is directed through said first aperture and travels along said top surface towards said second aperture.

13. A method for notifying a user of an end portion of a dental floss, said method comprising the steps of:
- a. providing a unitary and flexible core member having an elongated shape provided with opposed first and second ends, said first end defining a beginning segment of the core member and said second end defining an ending segment of the core member;
- b. covering said second end with a multi-colored outer coating surrounding an entire circumference thereof, said first end having an exposed outer surface spaced from said multi-colored outer coating such that said beginning segment remains uncolored, said core member having an annular cross-section extending along an entire longitudinal length thereof; and
- c. impregnating said multi-colored outer coating with a plurality of colored agents juxtaposed along a longitudinal length of said second end.

14. The method claim 13, wherein said multi-colored outer coating has a uniform thickness concentrically situated about said core member.

15. The method of claim 13, wherein said multi-colored outer coating is directly engaged with said core member and continuously extends along said second end such that said core member is invisible along said second end.

16. The method of claim 13, wherein said multi-colored outer coating is formed from at least two separate color dyes evenly distributed along an entire length of said second end.

17. The method of claim 13, further comprising:
- a housing providing with a bottom cavity; and
- a spool statically seated within said housing, said core member being concentrically wound about said spool and channeled upwardly therefrom.

18. The method of claim 17, wherein said housing further comprises:
- a planar top surface spanning across an entire top side of said cavity, said planar top surface being provided with a plurality of apertures formed therein;
- a cutting implement directly attached to said top surface and nested within a first one of said apertures, said cutting implement being located downstream of a second one of said apertures and further including an orifice formed therein such that a continuous passageway is formed between said cavity and an exterior of said top surface for collecting particulate portions of said multi-colored dental floss after being separated by said cutting implement; and
- a lid pivotally attached to said top surface;
- wherein said core member is directed through said first aperture and travels along said top surface towards said second aperture.

* * * * *